United States Patent [19]

Blickle

[11] Patent Number: 4,640,750
[45] Date of Patent: Feb. 3, 1987

[54] PROCESS FOR THE PREPARATION OF 3-HYDROXY-3-METHYLGLUTARIC ACID

[75] Inventor: Peter Blickle, Kelkheim, Fed. Rep. of Germany

[73] Assignee: Hoechst Aktiengesellschaft, Fed. Rep. of Germany

[21] Appl. No.: 801,761

[22] Filed: Nov. 26, 1985

[30] Foreign Application Priority Data

Nov. 28, 1984 [DE] Fed. Rep. of Germany ....... 3443303

[51] Int. Cl.$^4$ ............................................... C25B 3/02
[52] U.S. Cl. ...................................................... 204/79
[58] Field of Search ........................................ 204/79

[56] References Cited

U.S. PATENT DOCUMENTS 3,316,162  4/1967  Heuse et al. ........................... 204/79

FOREIGN PATENT DOCUMENTS 0082344  6/1983  European Pat. Off. .
841629   4/1980  U.S.S.R. .................................. 204/79

OTHER PUBLICATIONS

D. G. Hoare and W. A. Waters, Part IV, Kinetic Product Studies of Oxidations of Tertiary Alcohols, pp. 2252–2560.
K. Murayama and K. Murakami, Bulletin of the Chemical Society of Japan, vol. 41, pp. 1401–1404.
J. Kaulen and H. J. Schafer, Tetrahedron, vol. 38, No. 22, pp. 3299–3308 (1982).
E. Sokolova, Elektrochimichi Acta 1975, vol. 20, pp. 323–330.

Primary Examiner—R. L. Andrews
Attorney, Agent, or Firm—Finnegan, Henderson, Farabow, Garrett & Dunner

[57] ABSTRACT

3-Hydroxy-3-methylglutaric acid is prepared by electrolysis of an aqueous alkaline solution of 3-methyl-1,3,5-pentanetriol using anodes coated with nickel oxide/hydroxide NiO(OH) and conventional cathodes, followed by acidification of the alkaline solution and conventional working up. The yields achieved by this are always between about 70 and 85% of theory.

3 Claims, No Drawings

PROCESS FOR THE PREPARATION OF 3-HYDROXY-3-METHYLGLUTARIC ACID

3-Hydroxy-3-methylglutaric acid is the compound of the formula

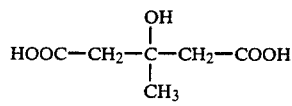

Because of its biological activity (reducing blood lipid and cholesterol levels) its principal importance is in the drugs sector.

The compound is obtainable in a relatively new process by oxidation of the—relatively readily accessible and commercially available—3-methyl-1,3,5-pentanetriol with permanganate in neutral or alkaline solution at temperatures between about 10° and 110° C. (European Pat. No. A-0082344). The process is based on the following equation (diagrammatic):

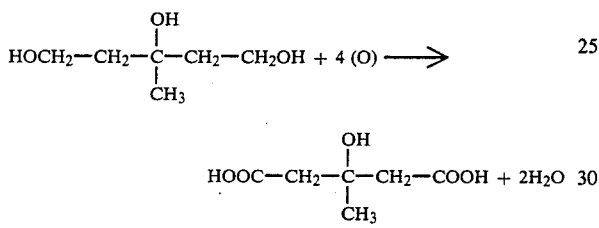

In the abovementioned European Patent, the yields of 3-hydroxy-3-methylglutaric acid obtainable by this process are termed "excellent"; however, the actual yield obtained in the only example is but 40 to 42% of theory.

According to the example, 3-methyl-1,3,5-pentanetriol was oxidized in aqueous alkaline solution with potassium permanganate, $KMnO_4$, in the temperature range between about 25° and 80° C., then the manganese dioxide, $MnO_2$, which had formed was filtered off, and the manganese dioxide was washed thoroughly with water and the collected filtrates were acidified with concentrated hydrochloric acid. The acidic solution was evaporated, extracted with acetone, and the acetone extract was concentrated, dissolved in acetonitrile, heated with anhydrous magnesium sulfate and with active charcoal, and filtered. The 3-hydroxy-3-methylglutaric acid crystallized out on cooling the filtrate.

Because the yield is not very high and because considerable amounts of manganese dioxide are produced, which is well known to be highly adsorbent and hardly able to be regenerated with acceptable effort, the process is, at least for industrial purposes, still in need of improvement.

It is known, from a study by J. Kaulen and H.-J. Schäfer (Tetrahedron Vol. 38, No. 22, pages 3299 to 3308 (1982)) that, inter alia, $\alpha,\omega$-diols such as, for example, 1,6-(n)-hexanediol or 1,10-(n)-decanediol are oxidized to the corresponding $\alpha,\omega$-dicarboxylic acids by electrolysis in alkaline solution using anodes coated with nickel oxide/hydroxide, NiO(OH), and steel cathodes, with yields of up to about 85% of theory. The oxidation is said to take place mainly by an indirect anode process in which the $\alpha,\omega$-diol is oxidized by the nickel oxide/hydroxide (with 3-valent Ni) as far as the carboxylic acid stage. During this, nickel oxide or hydroxide with only 2-valent Ni is produced from the nickel oxide/hydroxide (with 3-valent Ni). The 2-valent Ni is then converted back into the 3-valent stage by electron removal at the anode.

The abovementioned study by J. Kaulen and H.-J. Schäfer makes no report of the electrochemical oxidation of $\alpha,\omega$-diols which also have a tertiary hydroxyl group in the molecule. It is merely evident from the study, in addition, that in some of the anodic oxidations described there tert.-butanol was used as a cosolvent—and apparently underwent no change thereby.

However, this is not surprising because tert.-butanol is known to be extremely resistant to oxidative effects compared with other tertiary alcohols; cf. D. G. Hoare and W. A. Waters, J. 1962, pages 2552-2560. The oxidation experiments described in this article were carried out with compounds of 3-valent cobalt.

The substantial electrochemical inactivity of tertiary alcohols is also discussed in the article by E. Sokolova in Elektrochimica Acta 1975, vol. 20, pages 323-330. However, the article contains but little concrete data on the measurements of this, and these relate only to the single tertiary alcohol tert.-$C_5H_{11}OH$ (see page 324, right-hand column, line 3 from the bottom).

In this context, the study by K. Maruyama and K. Murakami "Cleavage reactions of alkoxy radicals produced by anodic oxidation of t-alcohols" in Bull. Chem. Soc. Japan, vol. 41, 1401-1404 (1968) appears more reliable. This study reports, with accurate measured data being given, the anodic oxidation of several tertiary alcohols (with elimination of hydrocarbon) to give the corresponding ketones.

In the attempt to make available an improved process, which is also practicable for industrial requirements, for the preparation of 3-hydroxy-3-methylglutaric acid, it has now been found that this object is achieved by electrolysis of alkaline solutions of 3-methyl-1,3,5-pentanetriol using anodes coated with nickel oxide/hydroxide.

Thus the invention relates to a process for the preparation of 3-hydroxy-3-methylglutaric acid by oxidation of 3-methyl-1,3,5-pentanetriol in aqueous alkaline solution, followed by acidification of the alkaline solution and customary working up, which comprises carrying out the oxidation by electrolysis using anodes coated with nickel oxide/hydroxide NiO(OH).

(Material) yields which are all between about 70 and 85% of theory are obtained with the process. In addition, the process is distinguished by being extremely straight-forward and environmentally acceptable; it does not entail the production of byproducts which pollute the environment. Thus the process represents a very considerable advance over that process of the state of the art which is probably the nearest for the preparation of 3-hydroxy-3-methylglutaric acid, according to European Pat. No. A 0082344 mentioned in the introduction.

It was very surprising, especially in view of the anodic oxidation of tertiary alcohols (with elimination of hydrocarbon) to give the corresponding ketones as known from the study by K. Maruyama and K. Murakami, loc. cit., that in the electrolysis according to the invention of the 3-methyl-1,3,5-pentanetriol the tert.-hydroxyl group is retained unchanged and hence that no ketone formation takes place during this.

In principle, the electrolysis is carried out in such a way that the aqueous electrolyte is electrolyzed on electrodes coated with NiO(OH). This coating is preferably carried out by a process proposed by McHenry (Electrochem. Technol. 5, 275 (1967)) for electrodes in Ni/Cd batteries. Layers produced in this manner are stable for many electrolyses and need not, like those described by Schäfer and Kaulen, be reactivated before each electrolysis. In principle, this entails first a Ni(OH)$_2$ layer being deposited cathodically from a Ni salt solution onto the future anode and then being converted anodically, in alkaline solution, into NiO(OH).

Apart from metallic nickel, it is also possible to use as the anode materials which are to be coated with NiO(OH) other materials to which the activated nickel oxide/hydroxide layer adheres, for example monel, stainless steel, graphite and vitreous carbon.

The cathode can be composed of any desired material which is customarily used in electrochemistry for the production of cathodes, such as, for example, noble metals, stainless steel or nickel.

The electrolysis cell can be composed of any desired material which is resistant to the electrolyte and the reactants. Thus, for example, alkali-resistant glass, porcelain, polyethylene, rubber and stainless steel are suitable.

The cell may be of the divided or undivided type; however the latter is preferred because there is no need to fear reduction of the desired product of electrolysis.

The process according to the invention can also be carried out continuously; however, it is preferably carried out discontinuously. In the latter mode, the electrolysis system is composed of an aqueous alkaline solution of 3-methyl-1,3,5-pentanetriol, with a pH preferably above 12. The alkalinity of the solutions is primarily brought about by alkali metal hydroxides (in particular NaOH and KOH). In practice, the alkali necessary for neutralization of the acid which is being produced is also added straightaway.

Advantageous 3-methyl-1,3,5-pentanetriol contents in the alkaline solution are between about 1 and 10, preferably between about 1 and 5, % by weight.

The electrolysis temperature is normally about 10° to 80° C., preferably about 15°–35° C.

It is also advantageous to carry out the electrolysis with a relatively large quantity of electricity—preferably about 1.2 to 2 times the theoretically required quantity.

After the electrolysis is complete, working up is carried out in a customary manner. For this purpose, the electrolyzed solution is brought to a pH of 1 to 2 with, for example, concentrated hydrochloric acid, and evaporated and the liberated 3-hydroxy-3-methylglutaric acid is then extracted with a suitable solvent. Suitable for this purpose are, for example, aliphatic ethers (diethyl ether, di-i-propyl ether, methyl tert.-butyl ether, etc.) Solvent is removed from the resulting extract and this provides 3-hydroxy-3-methylglutaric acid of good quality. There are hardly any losses on recrystallization (for example from butyl acetate).

The invention is now illustrated in detail by the examples which follow.

EXAMPLE 1

A solution of 46.6 g (0.348 mol) of 3-methyl-1,3,5-pentanetriol in 2.5 liters of 0.38N NaOH was electrolyzed, at 25° C. and 16 A for 7 hours (150% of the theoretically required quantity of electricity) at an electrode stack comprising 4 anodes (each 20×20 cm$^2$, nickel sheet coated on both sides with NiO(OH)) and 5 cathodes (each 20×20 cm$^2$, expanded metal of stainless steel) each 9 mm apart in a 3 liter glass trough. The electrolyzed solution was adjusted to pH 2 with 92 ml of concentrated hydrochloric acid, then concentrated to about 1000 ml and extracted with methyl tert.-butyl ether for 9 hours. Removal of the extractant in vacuo and recrystallization with butyl acetate provided 42 g of 3-hydroxy-3-methylglutaric acid (72.7% yield, melting point 108°–109° C.).

EXAMPLE 2

500 g (3.73 mol) of 3-methyl-1,3,5-pentanetriol in 10 liters of 1.1N NaOH were electrolyzed at 20° C. for 7.5 hours in a circulating electrolysis cell with a plate-electrode stack comprising 5 anodes (Ni plate coated on both sides with NiO(OH), total area 1 m$^2$) and 6 cathodes (stainless steel plates, total area 1 m$^2$) each 5 mm apart. The initial current strength of 130 A was reduced stepwise to 50 A until 150% of the theoretically required quantity of electricity had been reached. Working up was carried out in a manner analogous to that described in Example 1 and provided 492 g of 3-hydroxy-3-methylglutaric acid (81.4% yield, melting point 108°–109° C.).

I claim:

1. A process for the preparation of 3-hydroxy-3-methyl-glutaric acid by oxidation of 3-methyl-1,3,5-pentanetriol in aqueous alkaline solution, followed by acidification of the alkaline solution and conventional working up, which comprises carrying out the oxidation by electrolysis using anodes coated with nickel oxide/hydroxide NiO(OH).

2. The process as claimed in claim 1, wherein the electrolysis is carried out at a temperature between about 10° and 80° C.

3. The process as claimed in claim 1, wherein the electrolysis is carried out at a temperature between about 15° and 35° C.

* * * * *